United States Patent [19]

Arndt et al.

[11] 4,077,798

[45] Mar. 7, 1978

[54] SELECTIVE HERBICIDES

[75] Inventors: Friedrich Arndt, Aich; Gerhard Boroschewski, Berlin, both of Germany

[73] Assignee: Schering Aktiengesellschaft, Bergkamen and Berlin, Germany

[21] Appl. No.: 447,796

[22] Filed: Mar. 4, 1974

Related U.S. Application Data

[63] Continuation of Ser. No. 170,618, Aug. 10, 1971, abandoned.

[30] Foreign Application Priority Data

Nov. 24, 1970 Germany .............................. 2059309

[51] Int. Cl.$^2$ ................................................ A01N 9/12

[52] U.S. Cl. ..................... 71/100; 260/455 A; 71/98

[58] Field of Search ....................... 71/100; 260/455 A

[56] References Cited

U.S. PATENT DOCUMENTS

| | | |
|---|---|---|
| 2,977,209 | 3/1961 | Tilles et al. ............................ 71/100 |
| 3,404,975 | 10/1968 | Wilson et al. .......................... 71/100 |
| 3,632,332 | 1/1972 | Maeda .................................... 71/100 |
| 3,679,726 | 7/1972 | Kudamatsu et al. ................... 71/100 |
| 3,682,616 | 8/1972 | Kimura et al. ......................... 71/100 |
| 3,701,646 | 10/1972 | Neighbors .............................. 71/100 |

*Primary Examiner*—Glennon H. Hollrah
*Attorney, Agent, or Firm*—Joseph F. Padlon

[57] ABSTRACT

Substituted phenyl thiocarbamates and the method of producing them, are provided for selective weed control in cultivated grasses.

5 Claims, No Drawings

SELECTIVE HERBICIDES

This is a continuation of application Ser. No. 170,618, filed Aug. 10, 1971, now abandoned.

This invention relates to the use of substituted phenylthiocarbamates for selective weed control in cultivated grasses.

The herbicidal action of the 3-alkylcarboamoyloxy-phenylthiocarbamates, such as S-ethyl-N-(3-(n'-methyl-carbamoyloxy)phenyl-thiocarbamate is already known. This is noted from the German display document DOS No. 1,568,621. However, it was found that this active substance has no sufficient effect against grasses.

The object of the present invention is to eliminate the disadvantage of the known thiocarbamates and to provide a method for the selective control of undesired grasses, particularly in cultivated grasses.

This problem is solved according to the present invention by using compounds of the general formula

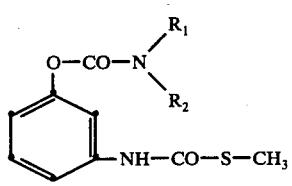

where R1 denotes a low alkyl and R2 phenyl, alkylphenyl, alkoxyphenyl, alkylthiophenyl or halogen phenyl, together with an inert vehicle and, if necessary, with the addition of surface active substances.

Grasses, particularly millets, such as *Setaria italica, Echinocloa crus galli* and *Digitaria sanguinalis,* were effectively controlled.

Surprisingly, the above indicated active substance show a high selectivity to cultivated grasses, particularly to rice plants, which are represented as grasses.

Since millets appear frequently as undesired grasses in rice-cultures, these millets can be controlled by using the above indicated compounds according to the invention, while at the same time leaving the cultivated grasses unharmed, thus representing a great technical advance.

The action of the above indicated active substances extends, however, not only to the above mentioned grasses but are also effective against many other weeds.

Thus, for example, dicotyledonous weeds, like *Stellaria media, Senecio vulgaris, Matticaria chamomilla, Lamium anplexicaule, Galinsoga parviflora, Centaurea cyanus, Amaranthus retroflexus, Chenopodium album, Ipomea purpurea, Chrysanthemum segetum,* and the like are effectively controlled.

The above indicated active substances according to the invention are preferably used in the postemergence method, that is, after the plants have emerged from the ground so that they are hit directly by the aqueous preparations of the active substances. But it is also possible to apply the preparations on the water surface of the flooded fields with the planted cultures.

The preferred amounts with the use of the invention in the post-emergence method are about 1-3 kg active substance/ha. Use in the pre-emergence method is likewise possible, but this requires amounts of more than 5 kg active substances/ha.

The above indicated active substances can be used in the form of preparations, as customarily used for herbicides, such as powders, pellets, solutions, emulsions or suspensions. Particularly suitable are emulsions with suitable additives.

As additives there can be used: inert, liquid and/or solid vehicles or diluants, as well as surface active substances, if necessary, like wetting, adhesive, emulsifying, and/or dispersing agents, as well as fertilizers or other substances.

Suitable liquid vehicles that may be used in conjunction with the invention such as xylene, cyclohexanol, cyclohexanone, isophorone, chloroform, carbon tetrachloride, dimethyl formamide, dimethyl sulfoxide, etc.

As surface active substances there can be used, anion active, cation- active and non iogenic substances, like ethoxylated nonylphenol, alkylphenol-polyglycolether, tributylphenyl polyglycol ether, alkylarylsulfates, alkylaryl polyether alcohols, isotridecyl alcohol, alkyl sulfates, lauryl ether sulfate, fatty alcohol ethylene oxide condensates, ethoxylated castor oil, polyoxyethylene alkyl ether, ethoxylated polypropylene, sorbite ester and lauryl alcohol-polyglycol ether acetal, etc.

These preparations can be produced in the usual manner such as by mixing or grinding. If desired, the individual components can be mixed shortly before use, as it is done in practice in the so-called tank mixing method.

The portion of active substances in the ready-to-use preparation can be 2 to 80% by weight, preferably 15 to 50% by weight of the preparation. In addition the preparations contain about 98 to 20% by weight, liquid or solid vehicles, as well as up to 20% by weight surface-active substances, if necessary.

The above indicated active substances can be used either alone or in mixture with other active substances. Other herbicides can also be used to widen the action spectrum, to improve the selectivity, the ground action, or to reduce the weather dependence with the compounds according to the invention.

Particularly suitable as additives are substances which can cause a synergistic effect, such as certain wetting agents, emulsifiers, solvents and non-phytotoxic oils etc.

In the above mentioned formula of the active substances of the invention it should be noted that desirable substituents particularly for R1 alkyl groups with 1 to 3 carbon atoms, and for R2 phenyl, 2-methylphenyl, 3-methylphenyl, 3-ethylphenyl, 4-ethylphenyl, 3-methoxyphenyl, 4-methoxyphenyl, 3-methylmercaptophenyl, 3-chlorphenyl, 3-fluorphenyl, 4-fluorphenyl, are included.

The hitherto unknown active substances can also be produced according to known methods, for example, from the corresponding chloroformic esters and aniline derivatives or from the corresponding phenols or their salts and carbamoyl chlorides adding inorganic or organic bases, or from the corresponding 3-nitrophenyl-N-alkyl-N-aryl-carbamates by hydrating the nitro group to the amino group, for example, by using Raney-nickel in methanol and subsequent reaction with chlorthioformic-S-methyl ester, if necessary, by adding an inorganic or tertiary organic base.

The production is thus effected by reacting compounds of the general formula

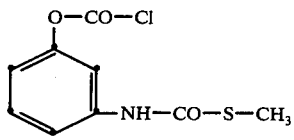

with an amine of the formula

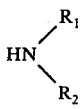

adding an inorganic or organic base, or by reacting compounds of the general formula

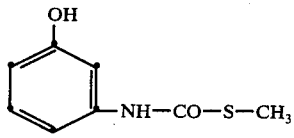

with carbamoyl chlorides of the general formula

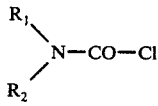

adding inorganic or organic bases, then by reducing compounds of the general formula

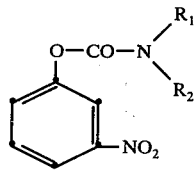

catalytically to the corresponding amine and reacting them subsequently with compounds of the formula

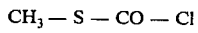

CH₃ — S — CO — Cl if necessary, by adding an inorganic or tertiary organic base to the desired end products, where R₁ and R₂ have the above indicated meaning.

The production of the compounds according to the invention will be described below.

PRODUCTION OF S-METHYL-N-(3-(N'-METHYL-N'-PHENYLCAR-BAMOYLOXY)PHENYL)-THIOCARBAMATE

A solution of 18.3 g (0.1 mole) 3-hydroxythiocarbanilic-S-methyl ester and 17.0 g (0.1 mole) N-methyl-N-phenylcarbamoyl chloride is heated in 50 ml dry pyridine for 45 minutes to 90° C. Then the product is evaporated in the vacuum, the residue is dissolved in methylene chloride, and the solution is washed successively with diluted soda lye, water, diluted hydrochloric acid, water and sodium-biscarbonate solution by adding ice. After drying with magnesium sulfate, the product is evaporated. From the initial oily residue are obtained from etherisopropyl ether 10 g (= 32 % of the theory) of a crystallate with a melting point of 101°–102° C.

PRODUCTION OF S-METHYL-N (3-N'-METHYL-N'-(4'-ETHYLPHENYL)-CARBAMOYLOXY)-PHENYL)-THIOCARBAMATE

To a solution of 10.8 g (0.08 mole) 4-ethyl-N-methyl aniline in 50 ml acetic ester are added in drops simultaneously with stirring and cooling to 10°–15 ° C, a solution of 19.6 g (0.08 mole) chloroformic-3-methylmercapto-carbonylamino-phenyl ester in 100 ml acetic ester and a solution of 11.1 g potassium carbonate in 50 ml water. The stirring in continued for 30 minutes without cooling, and then the organic phase is washed with diluted hydrochloric acid and water, adding ice. After drying with magnesium sulfate, the product is filtered in acetic ester over aluminum oxide (neutral) and evaporated in the vacuum.

Yield: 23.4 g = 85% of the theory.

After recrystallization from tetrahydrofurane/pentane, melting point 104°–108° C.

The chloroformic-3-methylmercapto-carbonylamino phenyl ester used as an intermediate product was produced in a known manner from the 3-hydroxythiocarbanilic-S-methyl ester and phosgene by adding dimethyl aniline in acetic ester.

In a similar manner there can be produced the following compounds for use according to the invention.

S-METHYL-N-(3-(N'-ETHYL-N'-(4'-METHYL-PHENYL)-CARBAMOYLOXY)-PHENYL)-THIOCARBAMATE

Melting point 104°–105° C.

S-METHYL-N-(3-(N'-ETHYL-N'-PHENYLCARBAMOYLOXY)-PHENYL)-THIOCARBAMATE

Melting point 158°–159° C.

S-METHYL-N-(3-N'-ETHYL-N'-(3'-METHYL-PHENYL)-CARBAMOYLOXY)-PHENYL)-THIOCARBAMATE

Melting point 100°–101° C.

S-METHYL-N-(3-(N'-ETHYL-N'-(2'-METHYL-PHENYL)-CARBAMOYLOXY)-PHENYL)-THIOCARBAMATE

Melting point 114°–116° C.

S-METHYL-N-(3-(N'-ISOPROPYL-N'-PHENYL-CARBAMOYLOXY)-PHENYL)-THIOCARBAMATE

Melting point 148°–149° C.

S-METHYL-N-(3-(N'-METHYL-N'-(3'-METHYL-PHENYL)-CARBAMOYLOXY)-PHENYL)-THIOCARBAMATE $N_D^{20}$ 1.5810.
$N_D^{20} = 1.5810$

The following example illustrates the invention.

EXAMPLE 1

The test plants listed below were treated in the hot house in the post-emergence method with the compounds to be used according to the invention in a dosage of 1 kg active substance/ha. The compounds were sprayed evenly as aqueous emulsions with 500 liter/ha. The reference compounds were used as aqueous emulsions likewise with 1 kg active substance/ha in 500 liter/ha.

The findings show that the compounds according to the invention permit a much better control of the undesired plants than the reference compounds.

The evaluation was made 3 weeks after the treatment.

| Compounds according to the invention | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| S-methyl-N-(3-(N'-methyl-N'-phenylcarbamolyoxy)-phenyl)-thiocarbamate | 10 | 0 | 0 | 0 | 0 | 0 | 0 | 0 | 0 | 0 | 0 | 0 | 0 | 0 |
| S-methyl-N-(3-(N'-methyl-N'-(4'-ethylphenyl)-carbamoyloxy)-phenyl)-thiocarbamate | 10 | 0 | 0 | 0 | 0 | 0 | 0 | 0 | 0 | 0 | 0 | — | 0 | — |
| S-methyl-N-(3-(N'-ethyl-N'-(4'-methylphenyl)-carbamoyloxy)-phenyl)-thiocarbamate | 10 | — | 1 | 0 | — | 0 | 1 | 0 | — | 0 | 0 | 3 | 0 | — |
| Reference compound | | | | | | | | | | | | | | |
| S-ethyl-N-(3-(N'-methylcarbamoyloxy)-phenyl)-thiocarbamate | 10 | 10 | 10 | 10 | 10 | — | 4 | 0 | 7 | 10 | — | 10 | 10 | — |

0 - totally destroyed, 10 - not damaged
1 - seed rice; 2 - sinapis esp; 3 - stellaria media; 4 - senicia vulgaris; 5 - matricaria chamomilla; 6 - lamium amplexicaule; 7 - centaurea cyanus; 8 - amarantus retroflexus; 9 - galium aparine; 10 - ipomea purpurea; 11 - chrysanthemum segetum; 12 - echinochloa crus galli; 13 - setaria italica; 14 - digitaria sanguinalis.

EXAMPLE 2

The test plants listed below were treated in the hot house in the same manner as described in Example 1. The results can be seen from the following table. These findings also show that the compounds used according to the invention are far superior in their herbicidal action than the reference compound, while leaving the cultivated plants unharmed.

| compounds according to the invention | 1 | 2 | 3 | 4 | 5 | 6 | 7 | 8 | 9 | 10 | 11 | 12 | 13 |
|---|---|---|---|---|---|---|---|---|---|---|---|---|---|
| S-methyl-N-(3-(N'-ethyl-N' phenyl-carbamoyloxy)-phenyl)-thiocarbamate | 10 | 0 | 0 | 0 | 0 | 0 | 0 | 0 | 0 | 0 | 0 | 0 | 0 |
| S-methyl-N-(3-(N'-ethyl-N'-(3'-methylphenyl)-carbamoyloxy)-phenyl)-thiocarbamate | 10 | 0 | 0 | 0 | 0 | 0 | 0 | 0 | 1 | 0 | 1 | 0 | 0 |
| S-methyl-N-(3-(N'-ethyl-N'-(2'-methylphenyl)-carbamoyloxy)-phenyl)-thiocarbamate | 10 | 0 | 0 | 0 | 0 | 0 | 0 | 0 | 0 | 0 | 0 | 0 | 0 |
| S-methyl-N-(3-(N'-isopropyl-N'-phenylcarbamoyloxy)-phenyl)-thiocarbamate | 10 | 0 | 0 | 1 | 0 | 0 | 0 | 0 | 0 | 0 | 1 | 0 | 0 |
| S-methyl-N-(3-(N'-methyl-N'-(3'-methylphenyl)-carbamoyloxy)-phenyl)-thiocarbamate | 10 | 0 | 0 | 0 | 0 | 0 | 0 | 0 | 0 | 0 | 1 | 0 | 0 |
| Reference compound | | | | | | | | | | | | | |
| S-ethyl-N-(3-(N'-methylcarbamoyloxy)-phenyl)-thiocarbamate | 10 | 10 | 10 | 10 | 10 | — | 4 | 0 | 10 | — | 10 | 10 | — |

0 - totally destroyed, 10 - not damaged
1 - seed rice; 2 - sinapis ssp; 3 - stallaria media; 4 - senecio vulgaris; 5 - matricaria chamomilla; 6 - lamium amplexicaule; 7 - centaurea cyanus; 8 - amarantus retroflexus; 9 - ipomea purpurea; 10 - chrysanthemum segetum; 11 - echinochloa crus galli; 12 - setaria italica; 13 - digitaria sanguinalis.

We claim:

1. A method for the selective control of weeds and grasses in the presence of a growing crop of rice plants which comprises applying to said weeds, grasses and plants, without differentiation, a herbicidal composition consisting essentially of a compound having the formula

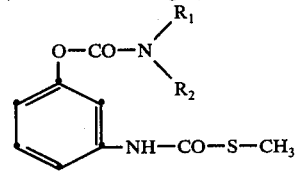

wherein $R_1$ is an alkyl group having from 1 to 3 carbon atoms and $R_2$ is selected from the group consisting of phenyl, 2-methylphenyl, 3-methylphenyl, 3-ethylphenyl, 4-ethylphenyl, 3-methoxyphenyl, 4-methoxyphenyl, 3-methylmercaptophenyl, 3-chlorophenyl, 3-fluorophenyl, and 4-fluorophenyl in an amount sufficient to substantially destroy said weeds and grasses without substantial damage to the rice plants.

2. The method of claim 1, wherein the herbicidal composition is applied post-emergent at a rate of about 1 to 3 kilograms of compound per hectare.

3. The method of claim 2, wherein said herbicidal composition consists essentially of from about 2 to about 80 weight percent of said compound, the balance being herbicidally inert.

4. The method of claim 2, wherein said composition consists essentially of from about 15 to 50 weight percent of said compound, the balance being herbicidally inert.

5. The method of claim 1 for the selective post-emergent control of millet in rice fields without substantial damage to rice plants wherein the herbicidal composition consists essentially of from about 2 to 80 weight percent of a compound defined in claim 1, the balance being herbicidally inert, said composition being applied to the field at a rate of from about 1 to about 3 kilograms of compound per hectare.

* * * * *